United States Patent
Jin et al.

(10) Patent No.: US 10,308,567 B2
(45) Date of Patent: Jun. 4, 2019

(54) PROCESSES AND SYSTEMS FOR OBTAINING AROMATICS FROM CATALYTIC CRACKING HYDROCARBONS

(71) Applicant: GTC Technology US LLC, Houston, TX (US)

(72) Inventors: Weihua Jin, Katy, TX (US); Zhongyi Ding, Katy, TX (US); Mircea Cretoiu, Sugar Land, TX (US); Joseph C. Gentry, Houston, TX (US); Mark Lockhart, Bellaire, TX (US); Calambur Shyamkumar, Missouri City, TX (US); Pinti Wang, Katy, TX (US)

(73) Assignee: GTC Technology US LLC, Houston, TX (US)

( * ) Notice: Subject to any disclaimer, the term of this patent is extended or adjusted under 35 U.S.C. 154(b) by 453 days.

(21) Appl. No.: 13/830,189

(22) Filed: Mar. 14, 2013

(65) Prior Publication Data

US 2014/0100398 A1    Apr. 10, 2014

Related U.S. Application Data

(60) Provisional application No. 61/711,934, filed on Oct. 10, 2012.

(51) Int. Cl.
| | |
|---|---|
| *C07C 2/76* | (2006.01) |
| *C07C 5/27* | (2006.01) |
| *C07C 15/08* | (2006.01) |
| *C10G 11/18* | (2006.01) |
| *C10G 35/04* | (2006.01) |
| *C10G 55/06* | (2006.01) |

(52) U.S. Cl.
CPC ............. *C07C 5/2729* (2013.01); *C07C 2/76* (2013.01); *C07C 5/2732* (2013.01); *C10G 11/18* (2013.01); *C10G 35/04* (2013.01); *C10G 55/06* (2013.01); *C10G 2300/1074* (2013.01); *C10G 2300/1077* (2013.01); *Y02P 20/52* (2015.11)

(58) Field of Classification Search
CPC combination set(s) only.
See application file for complete search history.

(56) References Cited

U.S. PATENT DOCUMENTS

| | | | |
|---|---|---|---|
| 5,609,751 A | | 3/1997 | Wall |
| 6,004,452 A | | 12/1999 | Ash et al. |
| 8,940,950 B2 | * | 1/2015 | Ellrich et al. .................. 585/319 |
| 2008/0287719 A1 | * | 11/2008 | Jan ............................ C07C 2/76 |
| | | | 585/418 |
| 2011/0319688 A1 | | 12/2011 | Ou |

(Continued)

OTHER PUBLICATIONS

C.S. (Sam) Kumar, Refining/Petrochemical Integration—A New Paradigm, Presentation at China Downstream Technology & Markets Conference, May 17 &18, 2011.*

*Primary Examiner* — In Suk C Bullock
*Assistant Examiner* — Ali Z Fadhel
(74) *Attorney, Agent, or Firm* — Winstead PC

(57) ABSTRACT

Methods and processes for producing paraxylene from catalytic cracking hydrocarbons, particularly $C_4$ and $C_{5+}$ streams, are disclosed. Each of the processing steps may be tailored to the overall objective of high paraxylene yield from a relative inexpensive feedstock.

20 Claims, 1 Drawing Sheet

(56) References Cited

U.S. PATENT DOCUMENTS

2012/0277506 A1\* 11/2012 Negiz .................... C10G 35/04
                                                        585/302
2014/0221714 A1\* 8/2014 Yanagawa .............. C10G 45/64
                                                        585/315

\* cited by examiner

PROCESSES AND SYSTEMS FOR OBTAINING AROMATICS FROM CATALYTIC CRACKING HYDROCARBONS

CROSS-REFERENCES TO RELATED APPLICATIONS

This Application claims the benefit under 35 U.S.C. § 119(e) of U.S. Provisional Patent Application Ser. No. 61/711,934 filed Oct. 10, 2012, which is incorporated herein by reference in its entirety as if fully set forth herein.

BACKGROUND OF THE INVENTION

Xylene isomers, orthoxylene (OX), metaxylene (MX), and paraxylene (PX), and ethylbenzene (EB) are $C_8$ aromatics from reforming process or other petrochemical processes. The purified individual xylene products are used on a large scale as industrial solvents and intermediates for many products. The most important isomer, PX, is used for the production of terephthalic acid (TPA) and dimethyl terephthalate (DMT), which are used for the production of fibers, films and polyethylene terephthalate (PET) bottles. In these applications high purity (>99.7%) PX is required. Demand for high purity PX has increased greatly over the past years to meet rapidly growing markets.

Traditional feedstock for aromatics and paraxylene production is catalytic reforming (reformate) or pyrolysis (pygas). Catalytic cracking, or fluid catalytic cracking (FCC), including various variations such as DCC, High-Severity FCC (HS-FCC), Residue FCC (RFCC), is another well-known process that produces fuels, light olefins, and a similar $C_6$ to $C_{10+}$ aromatics rich stream, known as catalytic naphtha, cat naphtha, or FCC gasoline.

Until recently, refiners did not consider recovering aromatics from FCC gasoline, because the extraction technology would not function with olefinic or sulfur impurities in the feed. There is a known technology which is designed specifically to make this operation by extraction, which permits the direct recovery of aromatics, while rejecting the olefin-rich fraction as raffinate. The sulfur species are also extracted into the aromatic fraction, which are removed in the downstream impurity removing step in the absence of olefins.

There is a known technology, namely Aromatization, to take olefinic hydrocarbon streams, as well as paraffinic or other type hydrocarbon streams, and produces BTX (benzene, toluene, and xylenes). This process technology will take any olefinic components in the $C_4$-$C_8$ range as feed to produce the aromatics. Byproducts are light paraffins and LPG off gases.

It is known to produce xylenes by methylation of toluene and/or benzene, for instance methylation of toluene over catalyst using methanol. The feedstock can be toluene, benzene, or a mixture of toluene and benzene, or a pygas feedstock, or a reformate feedstock, and the methylation product has higher paraxylene content than the paraxylene content of the feedstock.

There are other xylene formation technologies known to the industry which use benzene, toluene, $C_9$-$C_{10}$ aromatics, or a combination of them as feedstock. Examples of these are benzene/$C_9$-$C_{10}$ transalkylation, toluene/$C_9$-$C_{10}$ transalkylation, benzene/toluene/$C_9$-$C_{10}$ transalkylation, toluene disproportionation (TDP), selective toluene disproportionation (STDP).

To date, the art does not disclose a practical process for production of paraxylene from light catalytic cracking hydrocarbons and catalytic naphtha. In addition, the above processes have not been integrated into a single system that creates significant advantages, including higher xylene yields and lower energy consumption over operation of these processes separately.

In present invention, an improved process is disclosed which uses light and heavy hydrocarbons as feedstock particularly the light and heavy hydrocarbons from catalytic cracking unit, including, in embodiments, the combination of various streams and processes which provides significant advantages over prior systems.

SUMMARY OF THE INVENTION

In various embodiments, systems and processes for producing paraxylene from catalytic cracking hydrocarbons are disclosed. The methods comprise: 1) a separation section to separate $C_5$ and $C_{10+}$ from the $C_{5+}$ catalytic naphtha, which also includes one extraction zone to separate $C_6$-$C_9$ non-aromatics from $C_6$-$C_9$ aromatics; 2) an aromatization section to form aromatics from $C_4$-$C_9$ non-aromatics (or a subset) that contains significant amount of olefins; 3) providing an optional impurity removal section to clean the aromatics before they are sent to the downstream processes; 4) a second separation section to separate $C_6$-$C_7$, $C_8$, $C_{9+}$ streams, and to separate non-aromatics in the $C_6$-$C_7$ or $C_6$-$C_8$ stream to yield high purity aromatics, as final product or as feedstock for downstream paraxylene production section or xylene formation processes; 5) a xylene production section which includes paraxylene separation zone and xylene isomerization zone. The paraxylene separation zone can use crystallization method or adsorption method or a combination of these to produce high-purity paraxylene. The xylene isomerization zone can use EB-dealkylation type of catalyst or EB-isomerization type of catalyst to convert EB either to benzene or xylene; 6) optionally inclusion of a xylene formation section, which include one or more of the following processes: benzene methylation, toluene methylation, benzene/toluene methylation, benzene/$C_9$-$C_{10}$ transalkylation, toluene/$C_9$-$C_{10}$ transalkylation, benzene/toluene/$C_9$-$C_{10}$ transalkylation, toluene disproportionation (TDP), selective toluene disproportionation (STDP).

BRIEF DESCRIPTION OF THE DRAWINGS

For a more complete understanding of the present disclosure, and the advantages thereof, reference is now made to the following descriptions to be taken in conjunction with the accompanying drawings describing specific embodiments of the disclosure, wherein.

DETAILED DESCRIPTION OF EXEMPLARY EMBODIMENTS

Figures 1, 2:
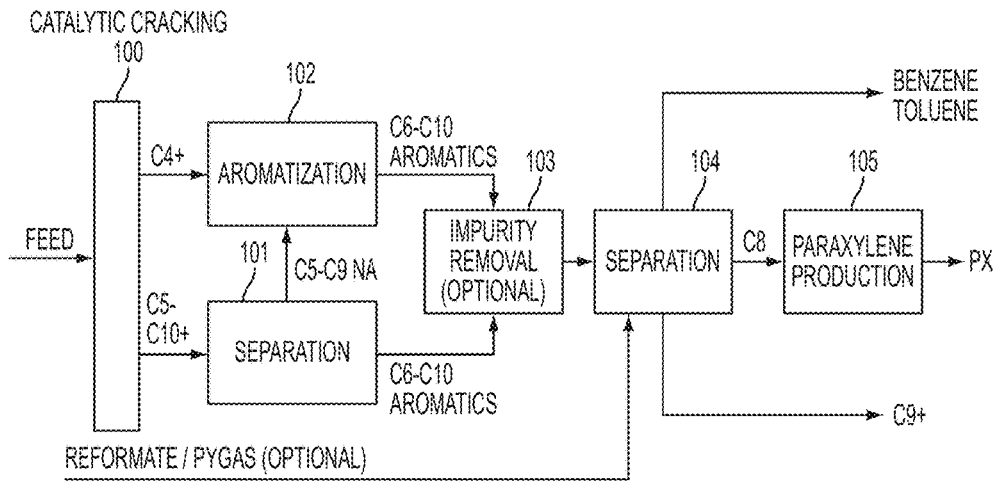
FIG. 1 shows an illustrative paraxylene production system from catalytic cracking $C_4$-$C_{10+}$ stream with option to include reformate and pygas feedstock in accordance with an embodiment of the invention.
FIG. 2 shows an illustrative paraxylene production system from catalytic cracking $C_4$-$C_{10+}$ stream with option to include reformate and pygas feedstock and additional xylene formation systems for additional paraxylene production in accordance with an embodiment of the invention.

In the following description, certain details are set forth such as specific feedstock, quantities, temperature, etc. so as to provide a thorough understanding of the present embodiments disclosed herein. However, it will be obvious to those skilled in the art that the present disclosure may be practiced without such specific details. In many cases, details concerning such considerations and the like have been omitted inasmuch as such details are not necessary to obtain a complete understanding of the present disclosure and are within the skills of persons of ordinary skill in the relevant art.

Fluid catalytic cracking is the most important conversion process used in petroleum refineries. It is widely used to convert the high-boiling, high-molecular weight hydrocarbon fractions of petroleum crude oils to more valuable gasoline, olefinic gases, and other products. There are different variations of the technology for different purposes, and there is a trend to increase the cracking severity to increase propylene yield from the system. High-severity FCC is intended to increase olefin yields, driven by the fast growing global demand for propylene. The propylene yields can be increased from 3-5% in conventional FCC to 15-28% when these units are operated at high severity. In high-severity FCC operation, the aromatic content in the cracked naphtha product is 50-70%, which is suitable for aromatics recovery, but, it contains significant amounts of thiophenic sulfur impurities and is highly olefinic. For example, Sinopec/Shaw's Deep Catalytic Cracking (DCC) uses heavy hydrocarbon feedstocks, such as VGO, VR or VGO blended with DAO to produce light olefins (ethylene, propylene and butylenes), LPG, gasoline, and middle distillates etc.

Aromatics cannot be directly recovered at high purity by conventional distillation, because of the close-boiling components and azeotropes which form with the aromatics. Therefore, the aromatics are typically recovered by extraction with a selective solvent. This can be accomplished either by liquid-liquid extraction, or by extractive distillation. Extractive distillation offers better plant economics and flexibility, and is generally preferred for BTX purification.

Until recently, refiners did not consider recovering aromatics from FCC gasoline, because the extraction technology would not function with olefinic or sulfur impurities in the feed. The new technology is designed specifically to make this operation by extraction, which permits the direct recovery of aromatics, while rejecting the olefin-rich fraction as raffinate. The sulfur species are also extracted into the aromatic fraction, which are removed by hydrotreatment in the absence of olefins. Thus, there is very little hydrogen consumption and no octane loss. The hydrogenation unit is much smaller than conventional, and can be a simple HDS design or other means. The raffinate from the extraction unit can be sweetened in a conventional caustic unit, or used directly in the gasoline. However, the raffinate stream contains significant amount of olefins and is an ideal feedstock for aromatization process to produce aromatics.

The aromatization process takes olefinic hydrocarbon streams and produces BTX, with an aromatic yield approximating the concentration of olefins in the feed. This process technology will take any olefinic components in the $C_4$-$C_9$ range as feed to produce the aromatics. Byproducts are light paraffins and LPG off gases. The unit can take the FCC $C_4$ and $C_5$ cuts along with the $C_6$-$C_9$ raffinate from catalytic cracking naphtha extraction unit mentioned above as feed to add another aromatics increment.

In the process illustrated in FIG. 1, the catalytic cracking naphtha ($C_{5+}$ stream) is first sent to a Separation Section 101, where $C_5$ and $C_{10+}$ streams are separated from the rest by distillation. The $C_6$-$C_9$ stream is then sent to extraction zone to separate non-aromatics from aromatics. The extraction zone can use extractive distillation method or liquid-liquid extraction method. The $C_4$ stream from catalytic cracking unit and C6-C9 non-aromatics from Separation Section 101, along with other olefin rich feedstock (optional) are sent to the Aromatization Section 102 to produce aromatics. The Aromatization Section can contain one reactor or multiple reactors, and they can be fixed bed reactors or continuous regeneration (CCR) type reactor systems.

The aromatics from the Separation Section 101 and Aromatization Section 102 are sent to an Impurity Removal Section 103, which can be optional depending on the impurities presented in the combined aromatics feed to the section. The Impurity Removal Section 103 can include one or more of the following processes to remove different impurities: hydrogenation, adsorption, absorption, solvent extraction, etc.

The cleaned-up $C_{6+}$ stream from 103 is fed to a second Separation Section 104 to separate benzene, toluene, xylenes, $C_{9+}$. Optionally, traditional $C_{6+}$ feedstock can also be processed in this section, such as reformate and hydrotreated pygas. Usually $C_6$-$C_7$ streams are first separated by distillation and then fed to an aromatics extraction zone to separate non-aromatics from $C_6$ and $C_7$ aromatics. The separation of $C_6$-$C_7$ non-aromatics from aromatics can be done using an extractive distillation method, liquid-liquid extraction method, or other methods known to the industry. $C_6$-$C_7$ aromatics from the extraction zone can be further separated to obtain individual benzene and toluene product. $C_8$ and $C_{9+}$ are also separated from the $C_{6+}$ feed stream by distillation. Sometimes the $C_6$-$C_8$ stream is separated and fed to the aromatics extraction zone to purify $C_6$-$C_8$ aromatics. The $C_{9+}$ stream can be used elsewhere and $C_{8+}$ stream is sent to Paraxylene Production Section 105.

Production Section 105 includes two main zones: a paraxylene recovery zone and a xylene isomerization zone. The function of Paraxylene Production Section is to purify the paraxylene, and to convert non-paraxylene C8 aromatics to paraxylene. Two major methods can be used for paraxylene recovery: crystallization and adsorption. A third method is a combination of these two. Xylene isomerization zone can use EB-isomerization type of catalyst, or EB-dealkylation type of catalyst.

In the method illustrated in FIG. 2, it is similar to the method illustrated in FIG. 1 except for the addition of Xylene Formation Section 106. The second Separation Section 104 can be optional and in this section $C_9$-$C_{10+}$ stream is also separated from C9+ stream in the distillation zone, which can be used as feedstock for the Xylene Formation Section 106. The extraction zone in the second Separation Section 104 can be optional, as the $C_6$-$C_7$ stream is consumed in the downstream Xylene Formation Section and does not required high purity. The addition of the Xylene Formation Section allows utilization of the available benzene rings to form xylenes; the resulted xylenes are then recovered in the Paraxylene Production Section. One or more of the following technologies or processes (but not limited to) can be included in the Xylene Formation Section: benzene methylation, toluene methylation, benzene/toluene methylation, benzene/$C_9$-$C_{10}$ transalkylation, toluene/$C_9$-$C_{10}$ transalkylation, benzene/toluene/$C_9$-$C_{10}$ transalkylation, toluene disproportionation (TDP), selective toluene disproportionation (STDP).

To save the number of pieces of equipment and investment cost, some of the equipment in one section can be shared with other sections. For example, the benzene and toluene columns in the distillation zone of the second Separation Section 104 can be shared with the transalkylation process in the Xylene Formation Section 106.

From the foregoing description, one skilled in the art can easily ascertain the essential characteristics of this disclosure, and without departing from the spirit and scope thereof, can make various changes and modifications to adapt the disclosure to various usages and conditions. The embodiments described hereinabove are meant to be illustrative only and should not be taken as limiting of the scope of the disclosure, which is defined in the following claims.

What is claimed is:

1. A process for producing paraxylene from a C4 stream and a C5+ catalytic naphtha stream from catalytic cracking unit, said process comprising:
    a) separating, in a first separation section, a C5-C9 non-aromatics stream and a first C6-C10 aromatics stream from the C5+ catalytic naphtha stream;
    b) forming, in an aromatization section, a second C6-C10 aromatics stream from the C4 stream, the C5-C9 non-aromatics stream, and an olefin rich feedstock;
    c) removing, via an impurity removal section, impurities from the first and second C6-C10 aromatics streams to create a purified C6-C10 aromatics stream;
    d) providing a reformate and pygas feedstock to a second separation section;
    e) separating, in the second separation section, a C6-C7 stream, a first C8 stream, a C9-C10 stream, a C11+ stream, and non-aromatics from the C6-C7 stream and the first C8 stream from the purified C6-C10 aromatics streams and the reformate and pygas feedstock;
    f) feeding the C6-C7 stream and the C9-C10 stream into a xylene formation section to form a second C8 stream; and
    g) feeding the first and second C8 streams into a paraxylene production section to produce a high-purity paraxylene product, the paraxylene production section comprising a paraxylene recovery zone and a xylene isomerization zone; and
    wherein the second separation section comprises a distillation zone that includes a benzene column and a toluene column, and wherein the xylene formation section of step f) shares the benzene column and the toluene column of the second separation section.

2. The process of claim 1, wherein step a) includes a distillation step and an extraction step.

3. The process of claim 2, wherein said extraction step is carried out by using extractive distillation method or liquid-liquid extraction method.

4. The process of claim 1, wherein step b) is carried out in a single reactor or multiple reactors that are fixed bed reactors or continuous regeneration (CCR) type reactor systems.

5. The process of claim 1, wherein said C5-C9 non-aromatics in step b) contains 15-85 wt % olefins.

6. The process of claim 1, wherein the removing of impurities in step c) is carried out using hydrogenation, adsorption, absorption, or solvent extraction, or a combination thereof.

7. The process of claim 1, wherein step e) includes a distillation step and an extraction step.

8. The process of claim 7, wherein said extraction step is carried out by using an extractive distillation or liquid-liquid extraction.

9. The process of claim 1, wherein xylene isomerization uses an EB-isomerization catalyst or an EB-dealkylation catalyst.

10. The process of claim 1, wherein the paraxylene recovery zone comprises crystallization and adsorption.

11. A process for producing paraxylene from a C4 stream and a C5+ naphtha stream from catalytic cracking unit, said process comprising:
    a) separating a feed stream into C4+ and C5-C10+ streams;
    b) distilling a C5-C9 non-aromatics stream and a C6-C10 aromatics stream from the C5-C10+ stream;
    c) feeding the C4+ stream, the C5-C9 non-aromatics stream, and a feed stream rich in olefins into a reactor to form aromatics from the C4+ stream and the C5-C9 non-aromatics stream;
    d) feeding an output stream from the reactor and the C6-C10 aromatics stream to an impurity removal section to remove impurities from the output stream and the C6-C10 aromatics stream;
    e) providing a reformate and pygas feedstock to a separation section;
    f) feeding an output stream from the impurities removal section into the separation section to separate the output stream and the reformate and pygas feedstock into a C6-C7 stream, a first C8 stream, a C9-C10 stream, a C11+ stream, and non-aromatics from the C6-C7 stream and the first C8 stream; and
    g) feeding the C6-C7 and the C9-C10 stream into a xylene formation section to form a second C8 stream; and
    h) feeding the first and second C8 streams into a paraxylene production section to produce paraxylene, the paraxylene production section comprising a paraxylene recovery zone and a xylene isomerization zone; and
    wherein the separation section comprises a distillation zone that includes a benzene column and a toluene column, and wherein the xylene formation section of step g) shares the benzene column and the toluene column of the separation section.

12. The process of claim 11, wherein step c) is carried out in a single reactor or multiple reactors that are fixed bed reactors or continuous regeneration (CCR) type reactor systems.

13. The process of claim 11, wherein said C5-C9 non-aromatics in step b) contains 15-85 wt % olefins.

14. The process of claim 11, wherein the removing of impurities in step d) is carried out using hydrogenation, adsorption, absorption, or solvent extraction, or a combination thereof.

15. The process of claim 11, wherein the separation section comprises a distillation step and an extraction step.

16. The process of claim 15, wherein said extraction step is carried out by using an extractive distillation method or a liquid-liquid extraction.

17. The process of claim 11, wherein paraxylene recovery is carried out by using crystallization or adsorption or a combination thereof.

18. The process of claim 11, wherein xylene isomerization uses an EB-isomerization catalyst or an EB-dealkylation catalyst.

19. The process of claim 11, wherein the production of xylenes uses benzene methylation, toluene methylation, benzene/toluene methylation, benzene/C9-C10 transalkylation, toluene/C9-C10 transalkylation, benzene/toluene/C9-C10 transalkylation, toluene disproportionation (TDP), selective toluene disproportionation (STDP) or a combination thereof.

20. The process of claim 11, wherein the paraxylene recovery zone comprises crystallization and adsorption.

* * * * *